(12) United States Patent
Sheldon et al.

(10) Patent No.: US 9,707,135 B2
(45) Date of Patent: Jul. 18, 2017

(54) DISPOSABLE ABSORBENT ARTICLE

(71) Applicants: Donald A. Sheldon, Downingtown, PA (US); Joseph Howard, Glenmoore, PA (US); William Terenzoni, Jamison, PA (US)

(72) Inventors: Donald A. Sheldon, Downingtown, PA (US); Joseph Howard, Glenmoore, PA (US); William Terenzoni, Jamison, PA (US)

(73) Assignee: Advanced Absorbent Technologies, LLC, Downingtown, PA (US)

( * ) Notice: Subject to any disclaimer, the term of this patent is extended or adjusted under 35 U.S.C. 154(b) by 72 days.

(21) Appl. No.: 14/204,616

(22) Filed: Mar. 11, 2014

(65) Prior Publication Data

US 2014/0276503 A1    Sep. 18, 2014

Related U.S. Application Data

(60) Provisional application No. 61/792,004, filed on Mar. 15, 2013.

(51) Int. Cl.
*A61F 13/53* (2006.01)
*A61F 13/537* (2006.01)
(Continued)

(52) U.S. Cl.
CPC .......... *A61F 13/5376* (2013.01); *A61F 13/42* (2013.01); *A61F 13/51113* (2013.01);
(Continued)

(58) Field of Classification Search
CPC .......... A61F 13/49007; A61F 13/49009; A61F 13/49017; A61F 13/49019;
(Continued)

(56) References Cited

U.S. PATENT DOCUMENTS 4,381,783 A    5/1983    Elias
4,695,278 A    9/1987    Lawson
(Continued)

FOREIGN PATENT DOCUMENTS

BE    EP 2444046 A1 *    4/2012    ......... A61F 13/5323
EP    0401189 A1    12/1990
(Continued)

OTHER PUBLICATIONS

Communication Relating to the Results of the Partial International Search for PCT/US2014/025963 mailed Aug. 14, 2014.
(Continued)

*Primary Examiner* — Lynne Anderson
(74) *Attorney, Agent, or Firm* — Caesar Rivise, PC

(57) ABSTRACT

A disposable absorbent undergarment is disclosed. It includes an absorbent assembly comprising a core formed of a synthetic tow or of synthetic nonwoven layers and having first section comprising a slow acting but high absorption capacity SAP and a second section comprising a fast acting but lower absorption capacity SAP, all of which is wrapped in a wrapper to hold the SAP in place. The absorbent assembly may be quilted and corrugated. The undergarment also includes releasably securable fasteners to enable it to be readily removed and a suspension system to ensure that the garment fits properly and doesn't leak even when holding a large amount of exudate. Odor removal/masking and treatment features may be provided. It addition the undergarment may include a wetness indicator.

30 Claims, 7 Drawing Sheets

(51) Int. Cl.
*A61F 13/42* (2006.01)
*A61F 13/511* (2006.01)
*A61F 13/534* (2006.01)
*A61F 13/535* (2006.01)
*A61F 13/531* (2006.01)

(52) U.S. Cl.
CPC .......... *A61F 13/534* (2013.01); *A61F 13/535* (2013.01); *A61F 13/537* (2013.01); *A61F 13/53436* (2013.01); *A61F 13/53747* (2013.01); *A61F 13/53752* (2013.01); *A61F 13/53756* (2013.01); *A61F 2013/424* (2013.01); *A61F 2013/5315* (2013.01); *A61F 2013/53024* (2013.01); *A61F 2013/53051* (2013.01); *A61F 2013/530226* (2013.01); *A61F 2013/530233* (2013.01); *A61F 2013/530306* (2013.01); *A61F 2013/53445* (2013.01); *A61F 2013/53472* (2013.01); *A61F 2013/530489* (2013.01); *A61F 2013/530518* (2013.01); *A61F 2013/530547* (2013.01); *A61F 2013/530562* (2013.01); *A61F 2013/530715* (2013.01); *A61F 2013/530722* (2013.01)

(58) Field of Classification Search
CPC ............ A61F 13/53436; A61F 13/5622; 13/5633; A61F 13/565; A61F 13/68; A61F 13/70; A61F 13/72; A61F 2013/49025; A61F 2013/49041; A61F 2013/49031; A61F 2013/530299; A61F 2013/530306; A61F 2013/530481; A61F 2013/530496; A61F 2013/530051; A61F 2013/530547; A61F 2013/530554; A61F 2013/530562; A61F 2013/530576; A61F 2013/5307; A61F 2013/530708; A61F 2013/530715; A61F 2013/530722; A61F 2013/530737; A61F 2013/530744; A61F 2013/5349; A61F 2013/53463; A61F 2013/53472; A61F 2013/5666; A61F 2013/5694; A61F 2013/588; A61F 2013/49087; A61F 2013/49088; A61L 15/60
See application file for complete search history.

(56) References Cited

U.S. PATENT DOCUMENTS

| | | | |
|---|---|---|---|
| 4,743,346 A | 5/1988 | Graham et al. | |
| 4,846,823 A | 7/1989 | Enloe | |
| 4,994,053 A * | 2/1991 | Lang | A61F 13/15634 428/117 |
| 5,055,103 A * | 10/1991 | Nomura | A61F 13/49009 604/358 |
| 5,163,932 A * | 11/1992 | Nomura | A61F 13/49009 2/401 |
| 5,415,644 A | 5/1995 | Enloe | |
| D362,120 S | 9/1995 | Suskind et al. | |
| 5,447,508 A * | 9/1995 | Numano | A61F 13/49011 604/385.27 |
| 5,599,338 A | 2/1997 | Enloe | |
| 5,762,641 A | 6/1998 | Bewick-Sonntag et al. | |
| 5,788,684 A * | 8/1998 | Abuto | A61F 13/532 604/358 |
| 5,938,650 A | 8/1999 | Baer et al. | |
| 5,977,014 A | 11/1999 | Plischke et al. | |
| 6,171,682 B1 * | 1/2001 | Raidel | A61F 13/15203 156/205 |
| 6,626,879 B1 * | 9/2003 | Ashton | A61F 13/496 604/385.01 |
| 6,689,115 B1 * | 2/2004 | Popp | A61F 13/49017 604/385.27 |
| 7,112,189 B2 * | 9/2006 | Otsubo | A61F 13/49001 604/201 |
| 7,765,614 B2 * | 8/2010 | Takino | A61F 13/496 2/111 |
| 7,887,522 B2 * | 2/2011 | Roe | A61F 13/496 604/385.01 |
| 8,257,334 B2 * | 9/2012 | Buell | A61F 13/496 2/400 |
| 8,646,506 B2 | 2/2014 | Ukegawa et al. | |
| 2003/0109840 A1 | 6/2003 | Dodge, II et al. | |
| 2003/0135177 A1 | 7/2003 | Baker | |
| 2003/0150551 A1 | 8/2003 | Baker | |
| 2005/0075617 A1 | 4/2005 | Vartiainen | |
| 2006/0069367 A1 | 3/2006 | Waksmundzki et al. | |
| 2006/0153984 A1 * | 7/2006 | Suzuki | A61F 13/15658 427/230 |
| 2006/0184146 A1 * | 8/2006 | Suzuki | A61F 13/535 604/358 |
| 2007/0032766 A1 * | 2/2007 | Liu | A61F 13/496 604/361 |
| 2008/0312628 A1 * | 12/2008 | Hundorf | A61F 13/15658 604/378 |
| 2011/0166540 A1 | 7/2011 | Yang | |
| 2013/0102982 A1 * | 4/2013 | Nakano | A61F 13/49019 604/365 |
| 2013/0284362 A1 * | 10/2013 | Tsujimoto | A61F 13/15617 156/276 |
| 2014/0276503 A1 | 9/2014 | Sheldon et al. | |

FOREIGN PATENT DOCUMENTS

| | | |
|---|---|---|
| EP | 0724418 B1 | 3/1999 |
| EP | 2679210 A1 | 1/2014 |

OTHER PUBLICATIONS

International Search Report for PCT/US2014/025963 mailed Dec. 3, 2014.
International Search Report for PCT/US2016/021310 mailed Oct. 20, 2016.

* cited by examiner

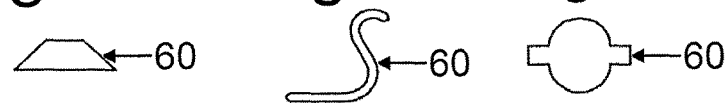
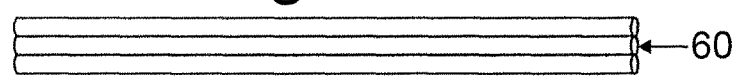
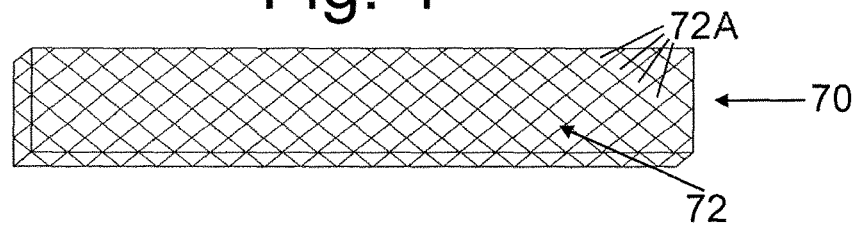
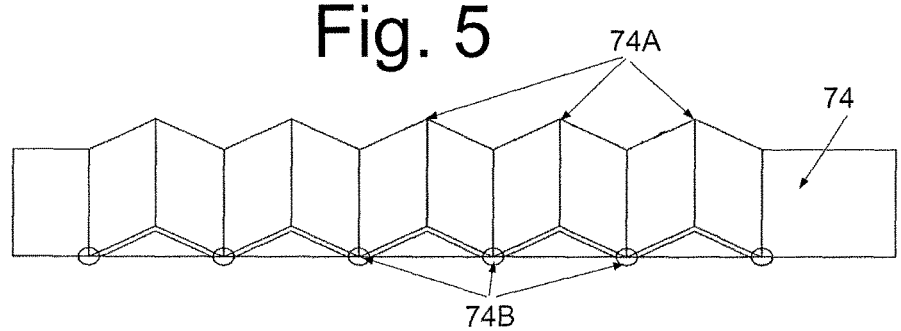

DISPOSABLE ABSORBENT ARTICLE

CROSS-REFERENCE TO RELATED APPLICATIONS

This application claims priority from provisional application Ser. No. 61/792,004, filed on Mar. 15, 2013, entitled Disposable Absorbent Article whose disclosure is specifically incorporated by reference herein.

FIELD OF THE INVENTION

This invention relates generally to disposable absorbent articles and particularly to disposable absorbent undergarments, e.g., adult briefs, protective underwear, bladder control pads, baby diapers and the like.

BACKGROUND OF THE INVENTION

Current adult disposable absorbent products, e.g., adult briefs, that exist in the market today utilize what is known as a fiberized bleached wood fluff pulp and a SAP (Super Absorbent Polymer) mixture for the absorbent core. At low ratio's of 30% or less SAP to pulp ratio, the core mixture may or may not be wrapped in an absorbent tissue to prevent the SAP from falling apart or out of the core. At higher levels of SAP at 50% or more, the core must be wrapped to prevent the loose SAP from being shaken out. Also a core adhesive may be added to prevent the heavier SAP particles from being separated from the fluff pulp fibers. This is the most advanced technology of today that is employed in infant sized disposable absorbent products. The pulp fiber in these products is required to rapidly manage the body fluid exudates until the SAP can desorb the fluff fibers to prepare the fluff fibers for the next exudates. For an infant, their body can produce up to 150 ml (grams) of urine and deliver it into the absorbent core over about 70 seconds. This delivery rate starts off rapidly and can achieve approximately 10 to 15 ml per second after the first 5 seconds or so and then trail down to zero. For an adult the amount of exudate is much larger and can easily exceed 300 ml or more delivered over a time period of more than 70 seconds at a rate similar or less than what infants void.

A significant problem with the current absorbent products that contain wood fluff pulp or even wrapped with a tissue or airlaid is in all cases their construction results in a core which feels wet against the body after it has received the voided fluid(s). This wetness feeling is akin to the feeling of wearing a cotton T-Shirt, getting it wet and then continuing to wear the wet cotton T-Shirt long after it should have been changed to a drier shirt. To address this wet feel, almost all current absorbent product designs employ a distancing layer of synthetic fibers on top of the "wet core" as an attempt to create a "feel drier" layer. This synthetic distancing layer is often called a "fluid transfer layer", "fluid acquisition layer", or "acquisition distribution layer (ADL)" and is typically much smaller than the core that it covers, leaving the edges of the core exposed. Moreover, despite their design goal, such fluid acquisition layers only work to a limited degree. In this regard as the exudate leaves the body at 98 degrees Fahrenheit it quickly drops to about 90 degrees Fahrenheit as it enters the core of the absorbent product. This creates a cooling affect when touched by the skin, which may increase during the time worn. If left on for an extended period of time, the wet product will achieve a thermal equilibrium and equilibrate somewhere between room temperature and about 90 degrees Fahrenheit, depending upon ambient temperature and clothes worn. This difference can be further exacerbated depending upon the thermal conductivity of the materials chosen to absorb the exudate. But in all cases current wood pulp fluff absorbent products will feel wet and/or cold to the skin the longer the product is worn.

The current state of the art product design for the synthetic absorbent cores is based upon a synthetic continuous fiber matrix inter-layered with superabsorbent particles (SAP). For example a polypropylene tow fiber similar to tow used in cigarette filter making was chosen. This material is purchased in a continuous form and is pulled out of the box and proceeds into an air trumpet or similar device or the like, to expand the fiber tow matrix. Then SAP particles are intermixed, adhesive is sprayed into the fiber SAP matrix and the entire matrix is wrapped to result in what is the state of the art of current "Pulpless" core technology. This type of core has the major limitations of a slow absorbency rate. That rate is highly dependent upon the SAP chosen and on the adhesive type and amount required to attach the SAP to the tow fiber matrix. For example, if enough adhesive is provided to ensure that the SAP remains in its desired location within the core, that adhesive may limit the SAP's absorbent swelling due to coating part of the SAP particles. If less adhesive is utilized, while it may permit greater swelling and absorption of the exudate by the SAP, it may allow the SAP particles to fall from their positions in the core to the bottom of the crotch area, rendering it heavier and wetter in the crotch area when voided into and less absorbents at the ends.

Another example of current pulpless core technology is gluing the SAP to the back sheet or inside the top or body facing sheet. This bonding process may limit the SAP from being fully expanded and utilized in absorbing the exudate.

Current SAP limitations require having to choose between a higher absorbent capacity, with the disadvantage of having slower speed, or a faster SAP with less absorbing capacity. If the current SAPs are mixed, the fast acting SAP will very rapidly swell and may "gel-block" the slower acting, but higher absorption capacity SAP. If gel-blocking occurs, it will limit, or even prevent, the higher capacity SAP from desorbing the faster but lower capacity SAP.

In the past a cellulose acetate fiber core with a single SAP has been developed and commercially available, as has a non-SAP version. Current polypropylene filament tow technology has also been used for the absorbent cores. In this regard, such polypropylene tow cores used in the market today make use of round or oval homo-polymer polypropylene fibers, which provide minimal resistance to fluid flow through the SAP/tow fiber matrix, thereby only providing minimal dwell time for the fluid to be absorbed by the SAP.

Thus, a need exists for a disposable absorbent product that is constructed so that the core will quickly and efficiently absorb the voided fluid, without leakage, and which will not feel wet, even when holding voided fluids over an extended period of time.

Another problem with existing absorbent products, such as undergarments, diapers and the like, is their ability to closely fit to the contours of the wearer and contain the voided fluids so that those fluids do not leak out. To that end, such products make use of various types of elasticizing designs. In particular, current elasticizing designs for disposable absorbent garments follow the same approaches as reusable underwear, which is that the waist band and waist areas are elasticized like conventional underwear, such as "Jockey" shorts, boxer Shorts or ladies panties. In addition, because these products are required to absorb exudates, elasticization of the leg area in the crotch area is required and appropriate. This results in two different elastic processes, materials and material applications, and product design approaches, which results in a more expensive and complicated design. This "crutching approach" results in early and premature leakage, i.e., leakage of the product below its potential total design capacity.

Moreover, the thickness of today's disposable absorbent products containing wood fluff pulp and the state of the art in pulp fiberizing technology result in an absorbent product that is significantly thicker than current cotton underwear. This results in a thicker product on the body which may not allow normal clothes or their usual size normal clothing to be worn. In addition the increased thickness of such products results in increased storage, transportation and handling costs and increased retail display space.

Current products today do not have any additional additives to address odor management, nor to reduce bed sores, rashes or irritations, other than depending upon SAP being present.

Accordingly, a need exists for an absorbent undergarment that addresses the above drawbacks of the prior art. The subject invention addresses those needs.

SUMMARY OF THE INVENTION

In accordance with one aspect of this invention an absorbent assembly is provided. The absorbent assembly is arranged for use in a product to be worn by a living being for absorbing and retaining exudates from the being. The absorbent assembly basically comprises a core formed of a plurality of fibers or nonwoven separation layers or combinations thereof having a multitude of interstitial spaces between the fibers or nonwoven layers. The core has a first section and a second section. The first section comprises at least a plurality of a slow acting but high absorption capacity SAP in fluid communication with the interstitial spaces or layers of nonwoven fabrics of the first section of the core. The second section of the core comprises a plurality of a fast acting but lower absorption capacity SAP in fluid communication the interstitial spaces or layers of nonwoven fabrics of the second section of the core. The first section of the core and the second section of the core are in fluid communication with each other. The absorbent assembly is arranged to be worn by the living being, e.g., incorporated into an undergarment, such as a brief, with the first section of the core forming a body-facing side disposed confronting the perineum region of the being and the second section of the core forming a remote side disposed away from the perineum region of the being. Fluid voided by the being is wicked to the fast acting SAP and to the slow acting SAP, wherein the fluid is absorbed quickly and rapidly by the fast acting SAP, while the slow acting SAP desorbs or takes fluid away from the fast acting SAP.

The core of the absorbent assembly may be formed of a synthetic tow, e.g., polypropylene tow, with the SAP either interspersed in the interstitial spaces in the tow and with the core wrapped in a wrapper, e.g., a non-absorbent, non-woven material, and quilted to ensure that the SAP doesn't migrate with respect to the core. Alternatively, the SAP may be secured on the surface of the tow, with the slow acting SAP on the body-facing side of the core, and with the fast acting SAP on the opposite side of the core.

Another alternative is to the separated SAP with a non-woven or tissue or airlaid or the like to prevent the SAP's two or more layers from intermingling. Or alternatively the SAPs may be separated with single or multiple layers of nonwoven which may or may not be wrapped.

In accordance with one preferred aspect of the subject invention the absorbent assembly forms a portion of a disposable absorbent garment, e.g., a brief. The wrapped core may be formed into a corrugated or otherwise undulating body having multiple peaks and valleys, with the absorbent assembly secured to the disposable undergarment at the valleys. The disposable absorbent garment may include a fluid acquisition layer disposed over the body-side of the core and interposed between the core and the being. It may also include an absorbent fluid management layer, e.g., absorbent tissue, air-laid or a softened or tenderized non-fiberized pulp sheet, or the like on the remote side of the core or in-between the SAP layers.

Further still, the disposable absorbent garment may include microencapsulated particles for reducing the odor of any fluid trapped in said assembly or masking such odor, wherein the microencapsulated particles have at least two levels of encapsulation such that all of said odor removing or masking agent is not released upon an initial fluid absorption by said absorbent assembly, but will be released upon a subsequent fluid absorption. The disposable undergarment may also include an anti-microbial treatment agent. Further yet, the disposable undergarment may include a wetness detector indicating when said absorbent assembly has absorbed fluid from the wearer.

In accordance with another preferred aspect of this invention a disposable absorbent undergarment, e.g., an adult brief, is provided. The undergarment basically comprises a chassis, an absorbent core, and a suspension system. The chassis comprises a sheet of a cloth-like, non-woven, breathable material, with the sheet having a front section, a back section, and an intermediate section. The front section includes a top front edge and pair of front side edges. The back section includes a top back edge and pair of back side edges. The intermediate section includes a pair of central side edges, each of which comprises an ergonomically shaped recess to form a respective leg opening for the brief. The absorbent core is located on the sheet at the intermediate section. The suspension system comprises plural elastic sections, each of those elastic sections comprises an apex end and a terminus end disposed generally opposite to the apex end. The width of the terminus end is substantially greater than the width of the apex end. The elastic sections are stretchable between the apex end and the terminus end, with the stretching force when the section is stretched being concentrated at the apex end and spread out along the width of the terminus end. A first of the elastic sections is secured to the chassis' sheet with the apex end of the first section being located at the recess in a first side edge of the chassis sheet and with the terminus end of the first section terminating adjacent the top front edge of the chassis sheet adjacent the first side edge. A second of the elastic sections is secured to the chassis' sheet with the apex end of the second section being located at the recess in a second side edge of the chassis' sheet and with the terminus end of the second section terminating adjacent the top front edge of the chassis' sheet adjacent the second side edge. A third of the elastic sections is secured to the chassis' sheet with the apex end of the third section being located at the recess in the first side edge of the sheet and with the terminus end of the third section terminating adjacent the back top edge of the chassis' sheet adjacent the first side edge. A fourth of the elastic sections is secured to the chassis' sheet with the apex end of the fourth section being located at the recess in the second side edge of the chassis' sheet and with the terminus end portion of the fourth section terminating adjacent the top back edge of the chassis sheet adjacent the second side edge.

That arrangement of the elastic sections enables the suspension system to pulls up on the chassis from its leg openings toward the top ends of the chassis when the undergarment is worn.

In accordance with still another preferred aspect of this invention a disposable absorbent undergarment, e.g., an adult brief, is provided. It basically comprises a chassis, an absorbent core, and a releasably securable fastening system. The chassis comprises a sheet of a cloth-like, non-woven, breathable material, the sheet having a front section, a back section, and an intermediate section. The front section includes a top front edge and pair of front side edges. The back section includes a top back edge and pair of back side edges. The intermediate section includes a pair of central side edges, each of which is an ergonomically shaped recess to form a respective leg opening for the undergarment. The absorbent core is located on the chassis at the intermediate section. The releasably securable fastening system comprises a cohesive coating located on the front side edges and a cohesive coating located on the back side edges. The cohesive coating on the front side edges is arranged to be releasably secured to the cohesive coating on the back side edges.

In accordance with yet another preferred aspect of this invention a disposable absorbent undergarment, e.g., an adult brief, is provided. It basically comprises a chassis and an absorbent core. The chassis comprises a sheet of a cloth-like, non-woven, breathable material, the sheet having a front section, a back section, and an intermediate section. The front section includes a top front edge and pair of front side edges. The back section includes a top back edge and pair of back side edges. Respective ones of the front side edges are secured to respective ones of the back side edges. The intermediate section includes a pair of central side edges, each of which is an ergonomically shaped recess to form a respective leg opening. The absorbent core is located on the chassis at the intermediate section. The top front edge and the top back edge are secured to each other along a seal line extending slightly below the top front edge and the top back edge to provide a finger grasping region above the seal line to enable a person to grasp the top front edge and the top back edge to break the securement of the secured side edges.

DESCRIPTION OF THE DRAWING

FIG. 4 is a plan view of a quilted core assembly constructed in accordance with this invention;

FIG. 5 is an isometric view of a portion of a corrugated core assembly constructed in accordance with this invention and shown secured to a chassis like the chassis of the brief shown in FIG. 1;

DETAILED DESCRIPTION OF THE PREFERRED EMBODIMENT

Figure 1:
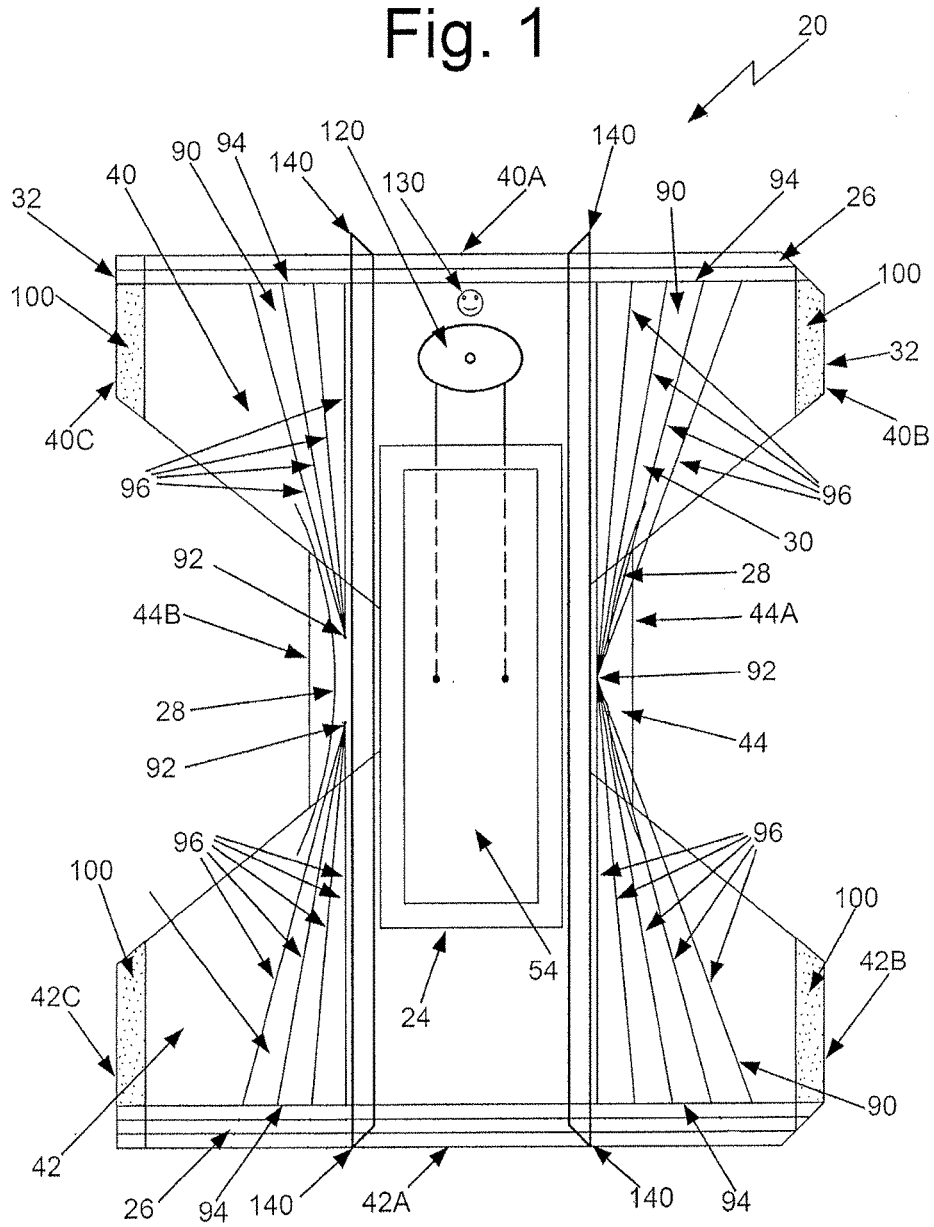
FIG. 1 is a plan view of one exemplary embodiment of a disposable absorbent article, in this case an adult brief, constructed in accordance with this invention, with the article shown opened up and laid flat showing its body-side.

Referring now to the various figures of the drawing wherein like reference characters refer to like parts, there is shown at 20 in FIG. 1 one exemplary embodiment of a disposable absorbent article, e.g., an undergarment. The undergarment 20 is in the form of a brief which is arranged to be worn by a person, e.g., an adult, under clothing to provide excellent fluid absorption and other capabilities in a construction that is comfortable to wear, easy to put on and take off, yet which is extremely thin so as to be virtually undetectable when worn under clothing.

It should be pointed out at this juncture that while the exemplary garment 20 of FIG. 1 is shown and described as being in the form of a brief for adults, it can be readily modified using many of the features which will be described later so that it is particularly suited for babies, e.g., is in the form of a diaper. In fact, with appropriate modifications the disposable absorbent article can be configured for use on pets. Moreover, and quite significantly, many of the various components of the disposable absorbent article, alone or in combination with each other are novel and provide significant utility for various other type absorbent products, e.g., feminine hygiene pads, panty liners, bandages, etc.

As best seen in FIG. 1, the brief, 20 basically comprises a chassis 22 and an absorbent assembly 24. The details of chassis 22 will be described later. Suffice it for now to state that the chassis 22 includes an elasticized waist band 26, an elastic suspension assembly 30 and a releasably securable attachment system 32. The exemplary undergarment 20 also includes an odor reducing system, a treatment system, and a wetness detecting system (all to be described later). The odor reducing system, the treatment system and the wetness detecting system may incorporated in the absorbent assembly or located elsewhere, e.g., in the chassis itself.

The chassis 22 basically comprises an outer sheet or shell and an inner sheet. The outer sheet or shell is formed of a cloth-like, non-woven laminated to a barrier film like material such as a 0.5 to a 0.9 mil polypropylene or polyethylene film. The film may be of a breathable material but needs to be liquid impermeable to prevent leakage, e.g., an extrusion coated SMS or the like. The inner sheet forms the "body-side" sheet of the chassis and is formed of a non-woven, breathable material, e.g., spunmelt polypropylene, or spunmelt polyethylene, or spunmelt polyester, or the like. The inner and outer sheets are similarly sized and shaped, with the inner sheet disposed over the outer sheet to form the chassis. The chassis includes a front section 40, a back section 42, and a central section 44. The front section includes a top front edge 40A and pair of front side edges 40B and 40C. The back section 42 includes a top back edge 42A and pair of back side edges, 42B and 42C. The central or intermediate section 44 includes a pair of central side edges 44A and 44B, each of which is a recess to form a respective leg opening for the brief when the side edges of the chassis are secured to each other to form the brief. Each leg opening is arranged to closely conform to the contiguous portion of the wearer's body in the interest of comfort and to minimize leakage of waste fluid from the brief. To further that end, the central side edges 44A and 44B forming the leg openings are elasticized to form the elastic leg cuffs (not shown). The details of the components making up the elasticized leg cuffs will be described later.

As is conventional, the portions of the chassis 22 contiguous with the front side edges 40B and 40C form what are commonly referred to as the front section "ears" of the chassis, while the portions of the chassis contiguous with the back side edges 42B and 42C form the back section ears of the chassis. The respective front section ears of the chassis are arranged to be overlapped somewhat by the respective back section ears of the chassis to be releasably secured together by the releasably securable attachment system 32 and thereby to form the respective leg openings of the chassis, when the brief is mounted in place on the wearer. The details of that releasably securable attachment system will also be described later.

Figure 2:
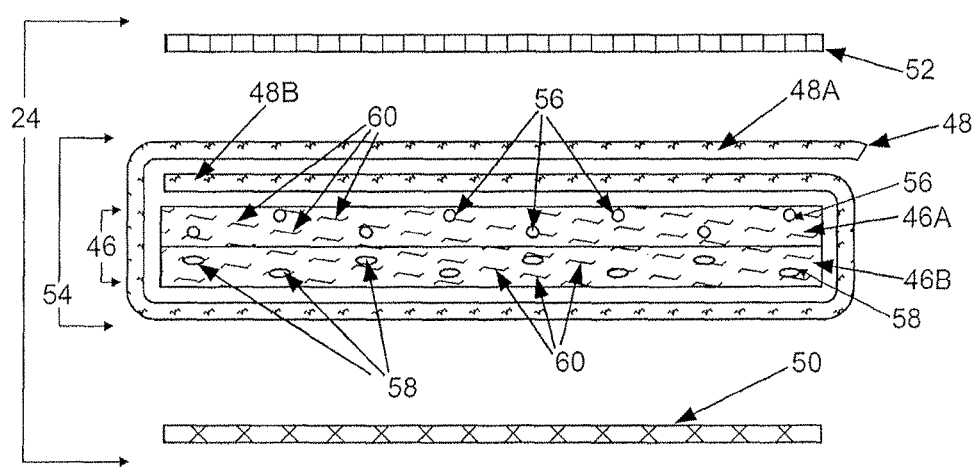
FIG. 2 is an enlarged sectional view of one exemplary absorbent assembly used in the brief of FIG. 1.

As best seen in FIG. 2 the absorbent assembly 24 basically comprises an absorbent core 46 and a wrapper 48. In the exemplary embodiment, the absorbent assembly also includes a cellulosic absorbent bottom fluid management layer (BFML) 50 (to be described later) and a fluid transfer or acquisition layer 52.

The absorbent core 46 is arranged to receive and retain voided fluid exudate, e.g., urine. It basically comprises a non-woven fiber construct to form a matrix in which at least two different performing SAPs or SAP blends are located. In accordance with one exemplary preferred aspect of this invention the core matrix is formed of a synthetic tow, or nonwoven or combinations thereof, e.g., polypropylene. A plurality of a slow acting, but high absorption capacity, SAP 56 and a plurality of a fast acting, but lower absorption capacity, SAP 58 are located either in or on the core matrix. The core matrix with the SAP 56 and SAP 58 is enclosed within the wrapper 48, whose construction will be described later, to form a core assembly 54.

The absorbent core 46 basically comprises an upper or "body-side" section 46A formed of a synthetic, e.g., polypropylene, tow and a lower section or "shell-side section" 46B formed of the same material. The total thickness of the core matrix 46 is approximately 10 mm, but could be thinner or thicker, depending upon the application for the absorbent assembly 24. The tow fibers making up the core extend generally parallel to the plane of the core, with a myriad of empty interstitial spaces located between the fibers of the tow for receipt of the fluid voided by the wearer of the garment 20. The slow acting, but high absorption capacity SAP 56 is located in the "body side" section 46A of the core and is dispersed within the interstices of the tow material making up that section of the core, while the fast acting, but lower absorption capacity SAP 58 is dispersed within the interstices of the tow material making up the shell-side section 46B of the core. The two sections 46A and 46B may be separate components of the same or differing material, or may be a unitary construction.

In another exemplary embodiment of an absorbent core 46 of this invention the slow acting SAP 56 is disposed (e.g., adhesively secured) onto the body-side surface 46A of a single or common core 46, while the fast acting SAP 58 is disposed (e.g., adhesively secured) onto the opposite shell-side surface 46B of the core matrix.

In either case, keeping the two types of SAP separate ensures that the core 46 will have both an acceptable absorbent rate and an acceptable total capacity. In particular, the fast acting SAP will absorb the fluid quickly and rapidly, while the slower, higher capacity SAP will desorb or take fluid away from the fast acting SAP, especially under pressure. Also one or both SAPs may be dyed, colorized or naturally non-white due to cross linker chosen to catalyze or cross link or neutralize the SAP, such as using ammonia based catalyst such as ammonium hydroxide ($NH_3OH$) instead of sodium hydroxide (NaOH). This could create a different core appearance than all white, but at a higher performance level.

Figure 3A:
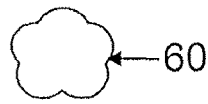
FIGS. 3A-3U are a series of respective, enlarged cross-sectional view of various shaped fibers that can be used in the core of the absorbent assembly of FIGS. 1 and 2
Figure 3B:
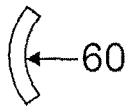
FIG. 3V is an isometric view of a shaped fiber that can be used in the core of the absorbent assembly of FIGS. 1 and 2.
Figure 3C:
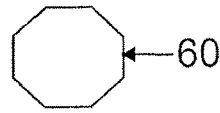
Figure 3D:
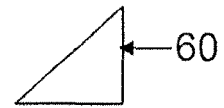
Figure 3E:
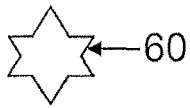
Figure 3F:
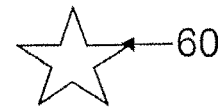
Figure 3G:
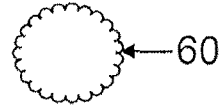
Figure 3H:
Figure 3I:
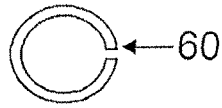
Figure 3J:
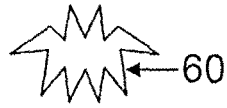
Figure 3K:
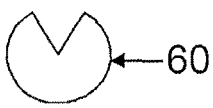
Figure 3L:
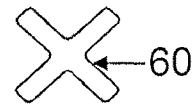
Figure 3M:
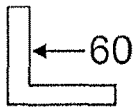
Figure 3N:
Figure 3O:
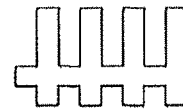
Figure 3P:
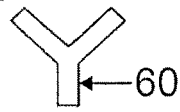
Figure 3Q:
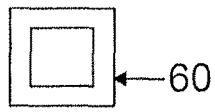
Figure 3R:
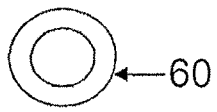

To increase the resistance of the core's fibers to fluid flow, the core's fibers may be shaped such as shown in FIGS. 3A-3U and 3V. In particular, the fibers of the core, which are designated by the reference number 60, can have a cross sectional shape of a smoothed pentagon, as shown in FIG. 3B. They can have a cross sectional shape of a curl, as shown in FIG. 3C. They can have a cross sectional shape of an octagon, as shown in FIG. 3F. They can have a cross-sectional shape of a triangle as shown in FIG. 3E. They can have a cross-sectional shape of a six sided star as shown in FIG. 3F. They can have a cross-sectional shape of a five sided star as shown in FIG. 3G. They can have a cross-sectional shape of a smoothed twenty four sided object as shown in FIG. 3H. Other cross-sectional shapes for the core's fibers are also contemplated, such as shown in FIGS. 3I-3V.

The fibers 60 can be shaped by the use of additives, such as an inorganic additive that will cause them to pucker or otherwise have a non-smooth surface. Alternatively, the fibers 60 may also be electronically treated with electricity or radiation to increase their surface texture. The purpose of these treatments is to increase resistance to fluid movement, delaying radial fluid wicking, to get more fluid wicking longitudinally and thereby increase utilization of the core.

An alternative embodiment of the core 46 entails the use of polyethylene or a bi-component polypropylene/polyethylene blend or even a tri-component fiber. Other combinations of multiple filament fibers may be appropriate to aid in enhancing fluid movement and wicking. Super absorbent fibers (SAF) may also be utilized in the core, but still should be utilized in conjunction with higher capacity SAP particles, as the SAF fibers have a lower capacity due to their inherent absorbency mechanism and nature.

As mentioned above, the core 46 is preferably wrapped within a wrapper 48 to form the core assembly 54. The wrapper serves to retain the SAP within the core 46 so that the SAP doesn't shake out or otherwise gain egress from the core. In particular, with a synthetic thermoplastic filament fiber core, the core is wrapped with a wrapper in the form of similar thermoplastic fiber netting, such as a spunbond polypropylene nonwoven with a basis weight of about 10 gsm. This could range down to about 8 gsm or may be increased to 13, 15, 20 or more gsm to ensure that the SAP will not fall out from the filament fiber matrix. By utilizing a thermoplastic wrapper instead of a tissue wrap (as has characterized the prior art which makes use of tissue wrap around a core having a single type of SAP therein), the core matrix and surrounding wrapper may be heat or ultrasonically sealed along plural bond or seal lines to quilt the construct and result in a quilted absorbent core assembly.

One exemplary example of a quilted absorbent core assembly is shown in FIG. 4 and is designated by the reference number 70. Thus, as can be seen in that figure the pattern of the quilting is in the form of a diamond pattern 72 comprising plural pockets 72A. The diamond pattern 72, or any other desired quilting pattern, can be formed by ultrasonically embossing (or using some other embossing technique, such as thermal, mechanical, adhesive embossing or the like) the wrapped core matrix. The ends of the wrapped core matrix may continue with the diamond quilt pattern or may be closed by a seal line along the edge of each end of the wrapped core. Ideally the diamond pattern bond area is no thicker than ⅛ inch in the weld area and the diamond patterns themselves are approximately one to two inches in length and approximately ½ inch in width, but wider or smaller designs may be utilized depending upon the desired product appearance. Although the diamond pattern is disclosed, other quilted designs that create respective pockets to prevent or minimize SAP movement through the matrix may also be utilized. In addition, the preferred bond itself is not continuous, but may be of an intermittent or discrete nature. In this regard, the bond lines only need to have adequate area coverage to ensure that no powdered dry SAP can shake out of the core. Thus, the bond strength only needs to be adequate to ensure that the dry SAP does not shake out, but may be weak enough to break when the SAP swells, either when it begins or nears full capacity. Such action ensures maximum utilization of all SAP, including the particles captured in the ultrasonic bond area. SAP may be captured in that area due to the thermoplastic properties of most SAPs utilized in absorbent products today. It is also contemplated to either quilt the entire absorbent core at one time or to aid in manufacturing, each SAP layer may be quilted separately, with or without the acquisition layer being in the quilted construction. Then depending upon the acquisition layer chosen to assist in fluid management, the two or more quilted layers may be aligned or not aligned over each other.

As best seen in FIG. 2, it is preferred that the wrapper 48 at the top layer of the absorbent core 46 facing the body side be of double thickness. Accordingly, the two end portions 48A and 48B of the wrapper 48 overlap each on top of the core. This aids in increasing the synthetic layer distancing from the body and could replace the need for the current fluid management layers, e.g., acquisition or transfer layers, found in current absorbent products. The double layer of the wrapper 48 on the body side of the core 46 also provides further distancing of the wet core from the body of the wearer, along with being an added layer to help prevent feeling the dry SAP particles.

As best seen in FIG. 1, the absorbent core assembly 54 is of a generally rectangular shape and extends over the intermediate portion of the chassis to encompass the insult zone adjacent the wearer's perineum, i.e., the zone at which the urine or feces, makes initial contact with the brief.

As mentioned earlier, a fluid transfer or acquisition layer 52 can be included in the brief 20. The fluid acquisition layer 52 is disposed on top of the wrapped core in the vicinity of the insult zone (adjacent the wearer's perineum). The fluid acquisition layer is utilized to facilitate and manage the transfer of the fluid waste material into the core. To that end, in the exemplary embodiment shown herein, the fluid acquisition layer 52 is also a rectangularly shaped member, which is smaller in width and length than the wrapped core. The fluid acquisition layer can be a single layer or multiple layers of any suitable material. The fluid acquisition layer may also be placed between the layers, under the layers or in multiple combinations thereof.

As also mentioned earlier, a cellulosic absorbent bottom fluid management layer (BFML) 50 can be included in the brief 20. In particular, it can be placed below the core assembly 54 (like shown in FIG. 2) so that if all the fluid is not fully absorbed by the SAP of the core 46 it will be captured by the BFML 50. The BFML is preferably rectangular in shape and may be formed of absorbent tissue, airlaid or a softened or tenderized non-fiberized pulp sheet. The airlaid may or may not contain additional SAP. The BFML layer should not be required as long as the blend of SAP in the core has at least one SAP that will adequately and rapidly absorb the initial voiding. Although less desired, the BFML may also be placed between the two SAP layers. In this configuration the BFML should allow the exudate to flow through to the fast layer for instantaneous absorption, but still allow the higher capacity body side SAP layer to assist in desorption of this middle layer as the middle layer assists in desorption of the lower layer.

In order to further increase the absorption capacity of the core assembly 54, it may be corrugated as shown in FIG. 5. In particular, the core assembly may be corrugated into a V-shaped construct 74 or some other undulating arrangement having peaks 74A and valleys 74B. The valleys 74B of the corrugated assembly are bonded, e.g., adhesively secured, the chassis at the areas shown by the small circles, e.g., to the inner surface of the outer shell of the chassis. This is an alternative to a flat full attachment coating to attach the core assembly to the back sheet. The well-known technique of micrexing may be used to produce the same result as corrugating and could be an additional process either before or preferably after ultrasonic pocketing or quilting of the wrapped SAP/fiber core. Then during the absorbency process the potential energy imparted to the core is rapidly converted to kinetic energy which will dramatically increase the speed of absorbency.

Figure 6:
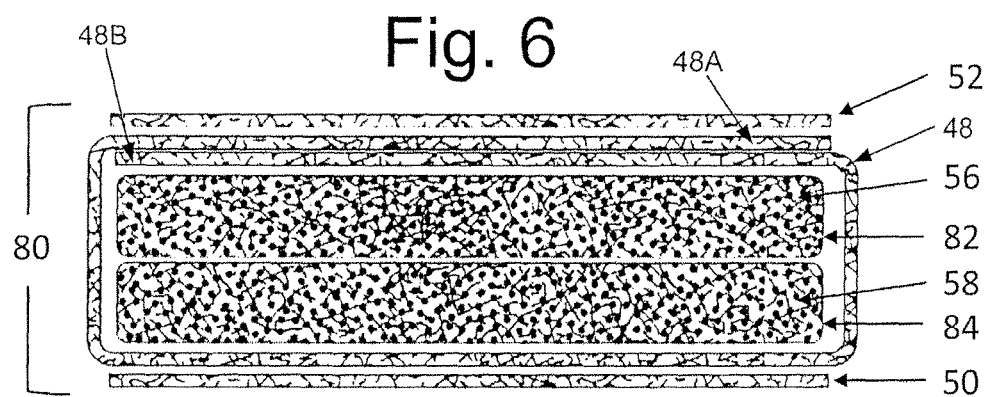
FIG. 6 is an enlarged sectional view, similar to FIG. 2, but showing another alternative embodiment of an absorbent assembly constructed in accordance with this invention.

An alternative embodiment of the above described tow core construction is to substitute a nonwoven acquisition layer, multiple nonwoven layers or similar materials in lieu of the polypropylene tow core. The purpose of this arrangement is to be mainly synthetic and heat or ultrasonically bondable and to provide some distance between the SAP particles. This alternative core construction is designated by the reference number 80 and is shown in FIG. 6. In such a construction, the core consists of two layers 82 and 84, which are separate layers (or which may be separate sections of a single layer which is folded to form the two layers shown). Like the embodiment of FIG. 2, two different SAPs are used in the core. One is a fast acting SAP 58, e.g., similar to the product sold as Aqua Keep 10SH "Instant Snow". The other is a slower acting, but high capacity SAP 56, e.g., similar to that is currently sold as Aqua Keep SA60, both manufactured by Sumitomo Seika. Ideally the two SAPs will be separated or positioned on either side of the two or more nonwoven material layers 82 and 84 making up the core 80. The core layers and the SAP may be electrically charged or adhesive added or even a water mist to get the SAP to stick to the fibers in the nonwoven material and further prevent the SAP from falling off or out of the core.

A wrapper 48, like that described above, encircles the SAP/core body and may be 8 to 15 gsm polypropylene or polyethylene spunbond or a spunbond/melt blown layer or the like that is ultrasonically bonded to provide integrity to the core material. Such ultrasonic bonding (or thermal, compression bonds or even adhesive bonding) is preferably used to create pockets or islands (not shown) holding the SAP in place to minimize and potentially prevent the SAP particles from congregating in the center of the folded core or along fold lines This latter condition may lead to gel blocking where the outside SAP particles take in fluid and prevent or starve the inner particles from receiving any fluid.

Figure 7:
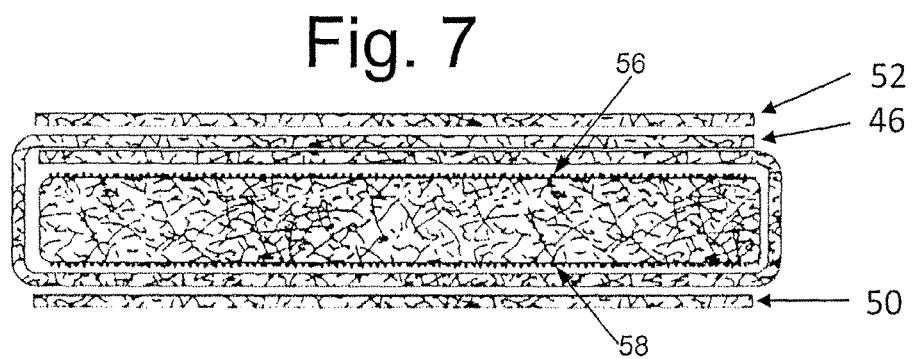
FIG. 7 is an enlarged sectional view, similar to FIGS. 2 and 6, but showing still another alternative embodiment of an absorbent assembly constructed in accordance with this invention.

Another alternative core construction is shown in FIG. 7. This embodiment is similar to the above embodiment of FIG. 6, except that the core comprises a single layer, with the SAP 56 added (e.g., adhesively secured) on top of the core layer and the SAP 58 added (e.g., adhesively secured) on the bottom of the core layer and with the wrap 46 extending about the SAP/core. The embodiments of FIGS. 6 and 7 may be further processed by corrugation, micrexing or the like as discussed above with respect to the embodiment shown in FIG. 5.

Figure 8:
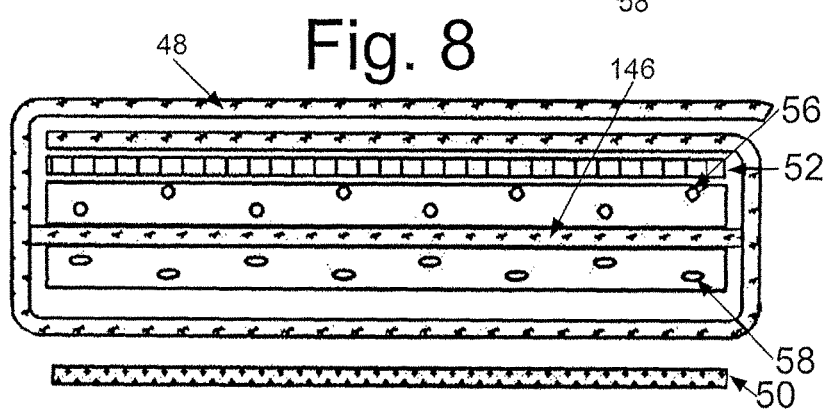
FIG. 8 is an enlarged sectional view, similar to FIGS. 2, 6 and 7 but showing another alternative embodiment of an absorbent assembly constructed in accordance with this invention.

Another alternative core construction is shown in FIG. 8. This embodiment is similar to the above embodiment except that the fluid acquisition 52 layer is positioned between the outer nonwoven wrap and the top of the absorbent core. In this design the upper core with the higher absorbent but slower SAP 56 is separated by a nonwoven layer 146 from the lower layer containing the faster SAP 58. This nonwoven separator may be equivalent to the nonwoven core wrap 46, for example a 10 gsm or similar material. Or may be another acquisition layer 52, for example of a 80 gsm or similar material or a nonwoven material with properties between these two basis weights, either alone or in conjunction with other nonwovens.

Figure 9:
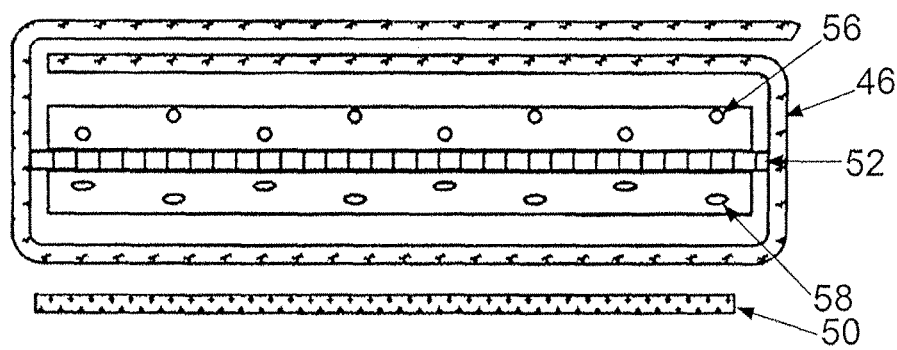
FIG. 9 is an enlarged sectional view, similar to FIGS. 2, 6, 7 and 8 but showing still another alternative embodiment of an absorbent assembly constructed in accordance with this invention.

Another alternative core construction is shown in FIG. 9. This embodiment is similar to the above embodiment showing the fluid acquisition layer in between the two layers of slower SAP 56 and the faster SAP 58. This is in place of or in addition to the nonwoven layers 146 discussed in FIG. 8.

Figure 12:
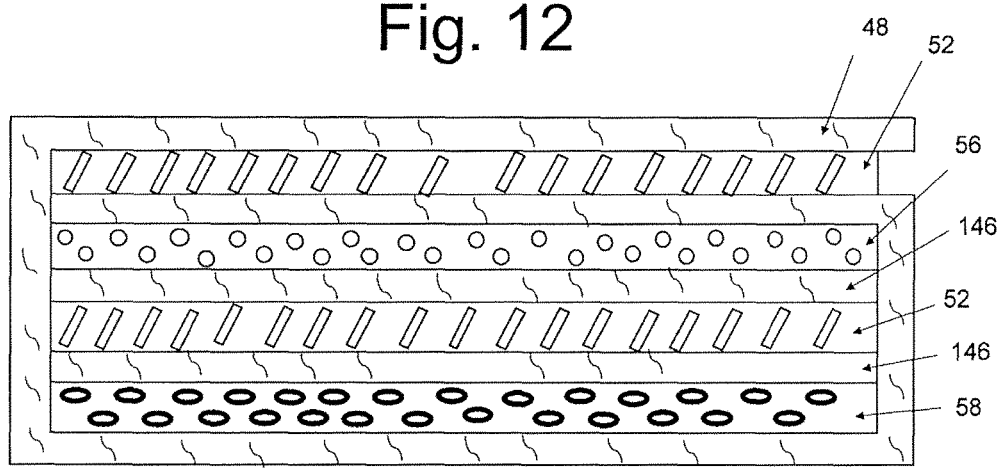
FIG. 12 is an enlarged sectional view, similar to FIGS. 2 and 6-9 showing still another alternative embodiment of an absorbent assembly constructed in accordance with this invention.

Another alternative core construction is shown in FIG. 12. This embodiment makes use of two acquisition layers 52. The first or top acquisition layer 52 is located between the overlapping portions of the wrapper 48. The second or bottom acquisition layer 52 is located between the two or more SAP layers 52 and 56, e.g., below the top SAP layer 56 and above the bottom SAP layer 58. Another alternative embodiment (not shown) makes use of an acquisition layer 52 under the core. As in the other constructions discussed above, the nonwoven wrapper 48 encompasses or wraps the entire core construction. To aid in keeping the SAP layers from intermingling, one nonwoven separation layer 146 is located between the top SAP layer 56 and the bottom acquisition layer 52 and another nonwoven separation layer 146 is located between the bottom acquisition layer 52 and the bottom SAP layer 58. Alternatively the SAP layers may be fully wrapped in a nonwoven wrapper 48 to aid in maintaining their separation in lieu of use of the two separation layers 146

Figure 10:
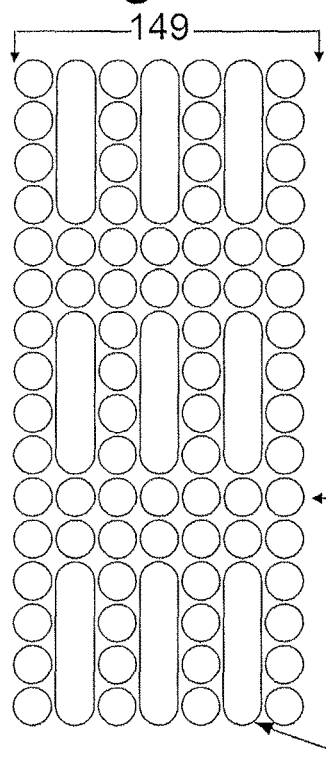
FIG. 10 is an enlarged top plan view of an alternative acquisition layer constructed in accordance with this invention.

Another alternative embodiment is to use a formed perforated film 149 in place of the nonwoven acquisition layer 52 as shown in FIG. 10. This material is composed of circles 150 and oblong ovals identified as 151. The ratio of length to width needs to be at least four to one, with one representing the size of the circle and narrowest width of the oblong oval. And four represents the length of oblong oval. Ideally this ratio would not exceed ten to one.

Figure 11:
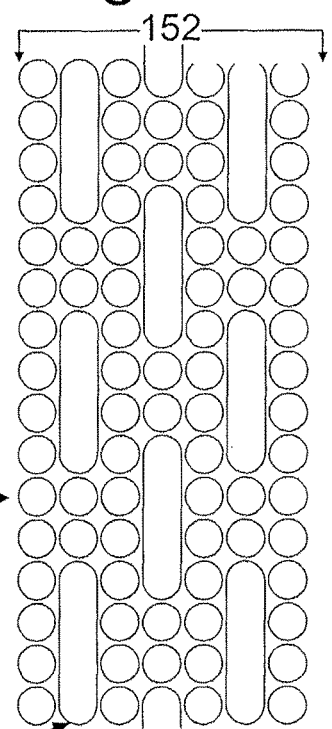
FIG. 11 is an enlarged top plan view of another alternative acquisition layer constructed in accordance with this invention.

Another alternative embodiment similar to FIG. 10 is represented in FIG. 11. This shows that the oblong ovals 151 do not need to be linearly aligned, but may be of an off-setting pattern or even in a random pattern.

The purpose of these oblong ovals is to aid in fluid penetration into the core. In may instances materials, for example, described in U.S. Pat. No. D362,120 and the like have only small holes or pores which when a urine voiding hits their surface, run off or leakage will occur. A novel solution to this problem is to have a mixture of smaller holes to aid in distancing from the wet core, while having an open area that will aid in rapid fluid penetration. If this material was made of exclusively of oblong ovals, it would not have the film strength and integrity to be processed on a production line. The combination of circles and oblong ovals solves this problem.

The film itself could be a two dimensional flat film with areas cut out as show in FIGS. 10 and 11. Ideally the film should be a formed three dimensional material with areas that may be cut out or vacuum formed but taking a warm film material and sucking it into a perforated screen of the desired pattern. But sucking the warm film into the screen, the film rapidly cools from the air that is pulled in and will leave the resulting film with a three dimensional perspective.

The ideal usage of such a novel formed perforated film is in place of the layer 52 in FIGS. 2, 6 and 7 included herein.

As should be appreciated the foregoing disposable absorbent articles constructed in accordance with this invention should exhibit improved thermal conductivity or heat transfer characteristics over the prior art. In a typical prior art fluff based designs, the predominately cellulosic core stays wet and therefore pulls heat from the body surface into the wet core which is usually at a temperature significantly lower than body temperature, but closer to ambient temperature. The absorbent articles of the subject invention keep a synthetic, all polymeric core closer to the body, thereby allowing the wetness from the voided fluid to be kept further from the body, resulting in a more comfortable product.

Another important feature of the absorbent undergarment 20 is its fit. As is known elastics are critical to fit of an absorbent undergarment and are directly related to leakage. If the undergarment is loose and baggy with gaps, when the person has voided into the undergarment, there may be leakage through these gaps. If the undergarment is too tight, it will be uncomfortable to put on and wear. Also critical is wet fit. An undergarment may have 300 to 600 ml (grams) of urine or more from two or more urinations that will cause the undergarment to have a tendency to slip and fall, which may cause leakage that could be embarrassing to the person wearing the undergarment.

Figure 13A:
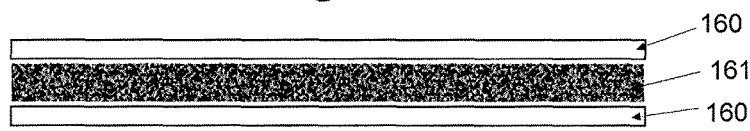
FIG. 13A is an isometric view of an elastic laminate showing it in its stretched state.
Figure 13B:
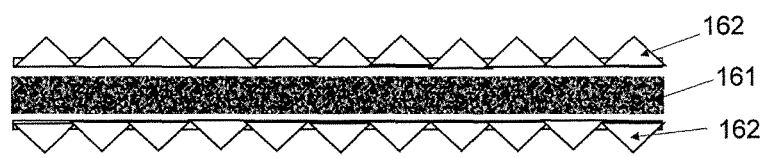
FIG. 13B is an isometric view, like that of FIG. 13A, but showing the laminate in corrugated or unstretched state.

Fit of the undergarments of this invention is addressed by usage of an elastic component encircling the waist area as shown in FIG. 1. In particular, the portion of the chassis contiguous with the front top edge 40A and the portion of the chassis contiguous with the back top edge 42A is elasticized so that when the ears of the chassis are secured to each other to form the brief, those elasticized portions of the chassis conjoin to form the elastic waistband 26. This elastic area may be extended into the hips and is composed of an elastic component, e.g., elastic filaments, films, netting or meltblown elastic materials or combinations thereof, laminated between the two sheets, i.e., the outer shell and the body-side sheet, making up the chassis 22. To further enhance the overall stretch of the side panels, the elastic laminate can be comprised of an outer non-stretchable nonwoven and an internal stretch component. In FIG. 13B, the laminate is shown in its relaxed or unstretched state in which the stretch component 161 relaxed, whereupon the nonwoven is corrugated (designated by the reference number 162). In its stretched state, as shown in FIG. 13A, the nonwoven is flattened (not corrugated) and is designated by the reference number 160. This enhanced stretch feature may be accomplished by Micrexing or knurling the non-stretchable nonwoven prior to laminating with the elastic center portion of the composite. This would potentially increase the overall stretch of the composite, but not aid in the elastic recovery. Another example is to add a small (e.g., about 1 to 10%, preferably 5%) of an elastic polymer such as Kraton or the like to the non-stretchable nonwoven to impart a small amount of stretch and potential recovery. The leg area is also elasticized by use of elastic strands or elastic film type materials to form a pair of leg elastics 28. In addition, the leg openings may be separately gasketed with respective elasticized leg cuffs 140. Such leg cuffs further impede urine flow and thus provide more time to allow the fluid acquisition layer to further spread out the fluid, thereby allowing the absorbent core additional time for the fluid to be absorbed.

In addition to the above elasticized portions of the undergarment, it also includes the heretofore identified suspension system 30. This system is also best seen in FIG. 1 and addresses the need for elastic support from a vector support approach. Like cabling on a bridge, the elastic ties into a point near the center of the leg cut out area 44A and 44B of the undergarment and radially moves outward and upward towards the area of the waist band 26. In particular, the suspension system comprises plural elastic sections 90 that originate in the crotch area and radiate outward and upward. Each of the elastic sections comprises an apex end 92 and a terminus end 94 disposed generally opposite to the apex end. The width of the terminus end 94 is substantially greater than the width of the apex end 92. The elastic sections 90 are stretchable between the apex end and the terminus end, with the stretching force when the section is stretched being concentrated at the apex end and spread out along the width of the terminus end. A first of the elastic sections 90 is secured to the chassis with the apex end 92 of the first section being located at the recess 44A in a first side edge of the chassis and with the terminus end 94 of the first section terminating adjacent the top front edge 40A of the chassis adjacent that first side edge. A second of the elastic sections 90 is secured to the chassis, with the apex end 92 of the second section being located at the recess 44B in a second side edge of the chassis and with the terminus end 94 of the second section terminating adjacent the top front edge 40A of the chassis adjacent the second side edge. A third of the elastic sections 90 is secured to the chassis, with the apex end 92 of the third section being located at the recess 44A in the first side edge of the chassis and with the terminus end 94 of the third section terminating adjacent the back top edge 42A of the chassis adjacent the first side edge. A fourth of the elastic sections 90 is secured to the chassis, with the apex end 92 of the fourth section being located at the recess 44B in the second side edge of the chassis and with the terminus end portion 94 of the fourth section terminating adjacent the top back edge 42B of the chassis adjacent the second side edge. This arrangement enables the suspension system 30 to pull up on the chassis 22 from the undergarment's leg openings toward the top ends of the chassis when the undergarment is worn and thus aids in pulling or resisting the normal tendency of the undergarment to fall or be pulled downward when normally worn, especially when loaded with voided fluid, like built-in suspenders. As mentioned above a normal void of fluid may add 150 ml to more than 300 ml (grams) of urine. If worn for a longer period, this amount can approach the theoretical capacity of the undergarment at over 1,000 ml (grams). This would be equivalent to more than 2½ pounds of weight exerted in the crotch area.

The elastic sections 90 of the suspension system 30 may be formed in various ways. For example, in the exemplary embodiment shown in FIG. 1 each of the elastic sections is formed of a plurality of elastic filaments 96 which spread out in a fan-shaped array from the apex end portion 92 to the terminus end portion 94. The filaments 96 of the two sections on each side of the undergarment may be continuous, if desired, so that they cross or nearly cross in the crotch area and are spread in the waist area. This later arrangement is particularly desirable to manufacture the undergarment by a continuous process. In accordance with one exemplary embodiment of the invention the filaments 96 are secured to the inner surface of the outer sheet or shell of the chassis.

Another alternative suspension assembly may make use of side panels, each with thick and thin areas of elasticity. This may be accomplished by using a material such as a vector stretch that is laminated between two sheets of spun-bond materials or the like, and are attached to the undergarment during the construction/manufacturing phase. This approach may also be utilized to enhance the current elastic technologies that are employed in both the elastic waist area and in the leg area. This elastic bridge may also be used in conjunction with leg cuffs like that described in U.S. Pat. Nos. 4,846,823, 5,415,644 and 5,599,338 assigned to Kimberly-Clark, and U.S. Pat. Nos. 4,695,278 and 4,743,346 assigned to Procter and Gamble, the disclosures of all of such prior art patents are incorporated by reference herein. In all cases the desired side panel material will have breathability to provide a vapor transmission rate of at least 100 grams per 24 hours.

Although the exemplary undergarment 20 described heretofore can utilize either a sealed or fused bonded edge, e.g., the side edges 40B and 42B and the side edges 40C and 42C being permanently secured to each other, as mentioned above a preferred embodiment of this invention makes use a releasably securable attachment system 32. That system will be described in detail later. Suffice it for now to state that the releasably securable attachment system basically comprise a pair of releasably securable side seals which allow the undergarment to be readily opened and checked by someone else for leakage. Use of such a releasably securable attachment system allows one to put on and take off the undergarment without removal of one's shoes and socks and the like. Heretofore undergarments, such as adult briefs, have made use of releasably securable fasteners, e.g., hook and loop attachment typically manufactured by companies such as Velcro USA, 3M or others. As will be appreciated by those skilled in the art, hook and loop fastening systems are expensive and the hooks themselves may be stiff, harsh and abrasive to the skin. Skin abrasion is less likely if the hook components are disposed facing. When hook components are facing inward, this creates the potential for the hooks to come in direct contact with the wearer's skin if the hook component is misfastened or if it should partially pop open. In either configuration, the hook components may also come in contact with any clothes used to cover over the absorbent garment. Adhesive tape systems have also been used in the past to impart re-fastenability. Such systems typically include an adhesive fastening tape and a landing zone for the tape. The adhesive tape itself is expensive and may be very stiff. The tape is composed of a film with an adhesive coated on one side and a release coating on the opposite side. This may also be used in conjunction with a release tape which is similar to the fastening tape in that it is a film with a release coating and an adhesive backing. The main difference between the two tapes is that the release tape is designed to bond to the absorbent article outer cover and the fastening tape is designed to bond to either the outer cover for a non-re-fastenable construction or to a landing zone if refasten ability is desired. The landing zone is also a tape material with an adhesive coating on the outer cover side and the relapse coating is designed to aid in re-fastenability. It may have a silicone or carbonate coating to aid re-fastenability.

The releasably securable fastening system 32 of the subject invention overcomes the above drawbacks of the prior art by making use of a cohesive coating in place of the bonded seal. In particular, an area on the inner surface of the ears of the body-side (inner) sheet of the chassis along the side edges 40B and 40C adjacent the front top edge 40A includes a cohesive adhesive coating 100 thereon, while a corresponding area on the outer surface of the ears of the shell or outer sheet of the chassis along the side edges 40B and 40C adjacent the back top edge 42A includes a similar cohesive adhesive coating 100 thereon. As is known a cohesive coating is an adhesive that only bonds to itself. Thus, the use of cohesive coating on these areas of the chassis enable them to releasably secure to each other when the ears are placed in an overlapping or abutting relationship to thereby provide the garment with re-fastenability, without the need for hooks, tapes or other extra or extraneous materials. Moreover, the cohesive portions of the chassis will only bond to themselves, not the outer clothing or to the skin of the wearer. This eliminates the need for films or other stiffing materials, improving comfort while reducing cost. Ideally this cohesive coating does not extend to the top of the undergarments waistband 26, but rather stops slightly short of the top to allow for gripping by fingers for ease of opening.

If the disposable undergarment is chosen to have bonded side panels rather than opening sides, then it is envisioned that the top edge is either left unbounded or a notch is added to aid in tearing the sides open. Ideally the unbounded top area is approximately 12 mm from the top, but at least 5 mm is required to aid in tearing open the sides. It would appear that approximately 25 mm would be too much which may allow waistband rollover, undesired in these products.

As is known, odor reducing technologies have been employed in absorbent undergarments with limited success and such technologies continue to perform poorly. When a person urinates, the urine releases ammonia and other ketones. Odor may be further increased depending upon medication, food eaten, etc. Past approaches to odor reduction have usually included adding strong fragrance and additives such as EDTA or sodium bicarbonate and the like to the undergarment. The fragrance is supposed to help mask the initial odor, but others may know that the wearer is wearing the product from the smell of fragrance. Moreover, once the fragrance evaporates, it is no longer a masking agent and its abilities are negated. Other approaches often used to mask odor usually address or attempt to prevent bacterial growth, which is another mechanism to reducing odor generation. This approach measures ammonia production by bacteria after a day or two. Anti-bacteria or bacterial growth inhibition practices do not address odor generation within the first four to six hours that an absorbent undergarment is normally worn. These approaches are only effective to reduce odor after disposal, such as once the undergarment is disposed and perhaps sitting in a trash can for a day or two.

The subject invention overcomes those drawbacks of the prior art by making use of an odor reduction system. In particular, that system basically comprises an odor reducer or masking agent, such as a fragrance, in microcapsules that dissolve when contacted with urine. To better manage odor reduction or management a preferred embodiment of this invention entails having the odor reducer or masking agent in microcapsules having at least two levels of encapsulation. In such an arrangement all of the fragrance or other odor masking or odor eliminating agent will not fully release or dissolve on the first contact with urine. This is of considerable importance with adult absorbent undergarments, such as briefs, as such products can be worn for two or three wettings. Thus, in accordance with one aspect of this invention half of the fragrance is microencapsulated with a single thickness designed to dissolve upon one wetting and the other half has a double coating designed to dissolve only after or upon the second wetting. The preferred fragrance can have a laundry fresh or Ultra Fresh fragrance to mask the odor of urine. Other fragrances, or a blend of fragrances, may be used as desired.

As is also known various treatments have been applied to diapers and incontinence products in the past with minimal success. In particular, surfactants have been used to aid in fluid penetration and other additives have been applied to the inner body side liner as an attempt to minimize and potentially prevent micro-ulcers or bedsores. Such treatments include Microban, other anti-microbial treatments and the like as an attempt to improve skin health and skin wellness. These materials are not very effective as they are usually added into the center of the body side contacting sheet or all over and they need to come in direct contact the perineum area. Direct contact with the perineum area does not usually happen as these types of undergarments typically lie flat against the buttocks.

The undergarment 20 of the subject invention overcomes those drawbacks of the prior art by making use of a treatment agent, e.g., elemental silver or a silver complex such as an oxide or carbonate, which is added into the spun-melt of the body side fabric sheet of the chassis 22. This fabric sheet may be produced from polypropylene or polyethylene or polyester or the like. If the additive is not applied into the spun-melt, then it may be applied topically or partially applied in both the spun-melt and on the surface. As desired, this may be used in conjunction with other anti-microbial odor reducing treatments, such as Ultra-Fresh SAB-40 produced by Thomson Research Associates Inc., and pH buffers when the buffers are incorporated as a low pH pulp, SAP or even other additives such as sodium bicarbonate or the like. This is the most effective process in managing the pH of the urine in contact with the skin.

The undergarment 20 also includes a wetness detector 120, which is preferably located in or in contact with the absorbent assembly and which forms a part of an electronic detection system (not shown). The wetness detector can comprise any suitable electronic component that is compact in size and comfortable to wear and which when in the presence of a conductive liquid conducts electricity to the electronic detection system. The electronic detection system does not form a part of the undergarment, although if desired it may be incorporated in the undergarment or as an adjunct thereto. The wetness detector can, for example, make use of wires or conductive inks or the like and act as a Wheatstone Bridge, completing a circuit in the electronic detection system to set off an alarm or the like when the wetness detector is in the presence of a conductive fluid, e.g., urine. This alarm signals either the user or anyone monitoring the product, such as a caregiver, nurse or a nurse's aide at a nursing home or a dementia unit, that the undergarment is wet. One issue with current wetness detecting systems is that disposable absorbent products, such as adult briefs, are designed to hold more than one wetting, usually at least two or three or more. If the undergarment is coupled to an electronic detection system which is activated after only one wetting, the undergarment will be underutilized and the consumer will pay substantially more money for products with these early alerts. What is preferred is a absorbent garment that will take at least two wettings before its wetness alarm system is activated. The subject invention accomplishes that end by utilizing a coating similar to the micro-encapsulated fragrances described above. As such activation of the alarm would require two urination wettings to dissolve the coating to activate the circuit. This is easier to accomplish in this invention in that it doesn't have a fiberized fluff core with the various adducts that arise from pulp when blended with urine. These would contaminate the circuit and make detection much more difficult.

In order to assist in opening a sealed edge of the undergarment to take the undergarment off, the very top portion or last ¼ inch may be left unbounded. This allows the user to more easily start ripping the side open for greater ease of changing and thereby also preventing pulling a soiled product down the legs and across the feet. Depending upon the condition of the user's hands, arthritic or the like, this unbounded area may be further increased, but should not exceed 1 inch.

Also to assist in determining if a product has experienced a wetness or urination, in the past visual wetness indicators have been employed to be viewed externally. This is appropriate if the product is not worn with any outer clothes, as is the case with infant diapers. This feature allows for the parent or caregiver to know that the product has been soiled. This would not be an appropriate design for adults either at home or in an assisted living facility or a nursing home, as adults wear outer clothing. To that end, a preferred embodiment of this invention, like the brief 20, includes a conventional wetness indicator 130. However, the wetness indicator 130 is mounted on the inside front of the undergarment adjacent the waist band. That way the user may pull the waist band outward and check to see if the product is wet with urine. This is especially important if the person has diabetes or other diseases which may limit the feeling of urination or coldness on the skin.

Without further elaboration the foregoing will so fully illustrate our invention that others may, by applying current or future knowledge, adopt the same for use under various conditions of service.

We claim:

1. An absorbent assembly for use in a product to be worn by a being for absorbing and retaining exudates from the being therein, said absorbent assembly comprising a core comprising:
   a) a first section having a predetermined width and length and being formed of a web of porous material configured to permit the migration of liquid therethrough, said web of porous material of said first section being quilted and comprising a plurality of a slow acting but high absorption capacity SAP located in respective pockets of said first section, whereupon said pockets of said quilted first section renders the SAP of said quilted first section resistant to migration with respect to said core;
   b) a second section located below said first section and having a predetermined width and length, said second section being formed of a web of porous material configured to permit the migration of liquid therethrough, said web of porous material of said second section being quilted and comprising a plurality of a fast acting but lower absorption capacity SAP located in respective pockets of said second section, whereupon said pockets of said quilted second section renders the SAP of said quilted second section resistant to migration with respect to said core, said first section of said core and said second section of said core being in fluid communication with each other, said absorbent assembly being arranged to be worn by the living being, with said first section of said core forming a body-facing side disposed confronting the perineum region of the being and said second section of said core forming a remote side disposed away from the perineum region of the being, whereupon fluid voided by the being flows to said fast acting SAP and to said slow acting SAP, wherein said fluid is absorbed quickly and rapidly by said fast acting SAP, while said slow acting SAP desorbs or takes fluid away from said fast acting SAP as well as absorbing said fluid itself; and
   c) an intermediate nonwoven fluid transfer layer having a predetermined width which is lesser than the predetermined width of said first and second sections, said intermediate nonwoven fluid transfer layer being located between said first and second sections to facilitate fluid transfer between said first and second sections.

2. The absorbent assembly of claim 1 wherein said porous material of said quilted first section of said core comprises a nonwoven material and wherein said porous material of said second quilted section of said core comprises a nonwoven material.

3. The absorbent assembly of claim 1 wherein said quilted first and second sections of said are ultrasonically embossed.

4. The absorbent assembly of claim 1 wherein said nonwoven material of said quilted first section is formed of spunbond polypropylene and said nonwoven material of said quilted second section is formed of spunbond polypropylene.

5. The absorbent assembly of claim 1 wherein said core additionally comprises super absorbent fibers (SAF).

6. The absorbent assembly of claim 1 additionally comprising a non-absorbent, fluid-pervious wrap disposed about said core.

7. The absorbent assembly of claim 6 wherein said wrap comprises thermoplastic fiber netting.

8. The absorbent assembly of claim 7 wherein said thermoplastic fiber netting comprises a spun-bond polypropylene nonwoven material.

9. The absorbent assembly of claim 6 wherein said wrap is overlapped to provide a double thickness layer at said body-facing side.

10. The absorbent assembly of claim 6 wherein said core with said wrap thereabout is quilted into a plurality of discrete pockets, each of said pockets serving to minimize or prevent SAP movement through said core.

11. The absorbent assembly of claim 10 wherein said quilted wrap is formed by a plurality of bonded lines, whose bond strength is strong enough to ensure that the SAP does gain egress from the respective pockets before the SAP absorbs fluid, but weak enough to break when the SAP absorbs fluid and swells.

12. The disposable undergarment of claim 6 additionally comprising a fluid acquisition layer disposed under said wrap.

13. The absorbent assembly of claim 1 wherein said assembly forms a portion of a disposable undergarment.

14. The disposable undergarment of claim 13 additionally comprising a fluid acquisition layer.

15. The disposable undergarment of claim 14 wherein said fluid acquisition layer is disposed over said body-facing side of said core.

16. The disposable undergarment of claim 14 additionally comprising absorbent fluid management layer on said remote side of said core.

17. The disposable undergarment of claim 16 wherein said absorbent fluid management layer comprises absorbent tissue, air-laid or a softened or tenderized non-fiberized pulp sheet.

18. The disposable undergarment of claim 13 additionally comprising an absorbent fluid management layer on said remote side of said core.

19. The disposable undergarment of claim 13 wherein said wrapped core is formed into a corrugated or otherwise undulating body having multiple peaks and valleys.

20. The absorbent assembly of claim 19 wherein said absorbent assembly is secured to said disposable undergarment at said valleys.

21. The disposable undergarment of claim 13 wherein said undergarment comprises microencapsulated particles for reducing the odor of any fluid trapped in said assembly or masking such odor.

22. The disposable undergarment of claim 21 wherein said microencapsulated particles comprise a desirable fragrance.

23. The disposable undergarment of claim 22 wherein said microencapsulated particles have at least two levels of encapsulation such that all of said fragrance is not released upon an initial fluid absorption by said absorbent assembly, but will be released upon a subsequent fluid absorption.

24. The disposable undergarment of claim 13 wherein said undergarment includes an anti-microbial treatment agent.

25. The disposable undergarment of claim 24 wherein said anti-microbial treatment agent comprises elemental silver, or a silver complex.

26. The disposable undergarment of claim 13 wherein said a disposable undergarment includes a wetness detector indicating when said absorbent assembly has absorbed fluid from the wearer.

27. The absorbent assembly of claim 26 wherein the wetness detector comprises a portion of an electronic wetness detection system.

28. A disposable absorbent undergarment comprising a chassis, an absorbent core, and a suspension system, said chassis comprising a sheet of a cloth-like, non-woven, breathable material, said sheet having a front section, a back section, and an intermediate section, said front section including a top front edge and pair of front side edges, said back section including a top back edge and pair of back side edges, said intermediate section including a pair of central side edges, each of which is an ergonomically shaped recess to form a respective leg opening for the brief, said absorbent core being located on said sheet at said intermediate section, said suspension system comprising plural elastic sections, each of said elastic sections comprising an apex end and a terminus end disposed generally opposite to said apex end, the width of said terminus end being substantially greater than the width of said apex end, said elastic sections being stretchable between said apex end and said terminus end, with the stretching force when said section is stretched being concentrated at said apex end and spread out along the width of said terminus end, a first of said elastic sections being secured to said sheet with said apex end of said first section being located at the recess in a first side edge of said sheet and with said terminus end of said first section terminating at said top front edge of said sheet adjacent said first side edge, a second of said elastic sections being secured to said sheet with said apex end of said second section being located at the recess in a second side edge of said sheet and with said terminus end of said second section terminating at said top front edge of said sheet adjacent said second side edge, a third of said elastic sections being secured to said sheet with said apex end of said third section being located at the recess in said first side edge of said sheet and with said terminus end of said third section terminating at said back top edge of said sheet adjacent said first side edge, and a fourth of said elastic sections being secured to said sheet with said apex end of said fourth section being located at said recess in said second side edge of said sheet and with said terminus end portion of said fourth section terminating at said top back edge of said sheet adjacent said second side edge, and wherein each of said elastic sections comprises a plurality of elastic fibers disposed in a fan shaped array, with said fibers diverging from each other from said apex end to said terminus end, whereupon said suspension system pulls up on said chassis from said leg openings toward said top ends when said undergarment is worn.

29. The disposable absorbent undergarment of claim 28 wherein said absorbent core comprises a plurality of fibers having a multitude of interstitial spaces between said fibers, said core having a first section and a second section, said first section comprising a slow acting but high absorption capacity SAP in fluid communication with said interstitial spaces of said first section of said core, said second section comprising a plurality of a fast acting but lower absorption capacity SAP in fluid communication with said interstitial spaces of said second section of said core, said first section being in fluid communication with said second section, said first section of said core forming a body-facing side and with said second section of said core being secured to said sheet, whereupon fluid voided by said being is wicked to said fast acting SAP and to said slow acting SAP, wherein said fluid is absorbed quickly and rapidly by said fast acting SAP, while said slow acting SAP desorbs or takes fluid away from said fast acting SAP.

30. An absorbent assembly for use in a product to be worn by a being for absorbing and retaining exudates from the being therein, said absorbent assembly comprising a core having a first section and a second section, said first section being formed of a web of porous material configured to permit the migration of liquid therethrough, said porous material of said first section comprising a nonwoven material, said web of porous material of said first section being quilted and comprising a plurality of a slow acting but high absorption capacity SAP located in respective pockets of said first section, whereupon said pockets of said quilted first section renders the SAP of said first section resistant to migration with respect to said core, said second section being formed of a web of porous material, said porous material of said second section comprising a nonwoven material configured to permit the migration of liquid therethrough, said web of porous material of said second section being quilted and comprising a plurality of a fast acting but lower absorption capacity SAP located in respective pockets of said second section, whereupon said pockets of said quilted second section renders the SAP of said second section resistant to migration with respect to said core, said first section of said core and said second section of said core being in fluid communication with each other, said absorbent assembly being arranged to be worn by the living being, with said first section of said core forming a body-facing side disposed confronting the perineum region of the being and said second section of said core forming a remote side disposed away from the perineum region of the being, whereupon fluid voided by the being flows to said fast acting SAP and to said slow acting SAP, wherein said fluid is absorbed quickly and rapidly by said fast acting SAP, while said slow acting SAP desorbs or takes fluid away from said fast acting SAP as well as absorbing said fluid itself, wherein said nonwoven material of said quilted first section is formed of a plurality of fibers, wherein said nonwoven material of said quilted second section is formed of a plurality of fibers, and wherein said fibers have a cross sectional shape having an increased surface area compared to circular or oval shaped fibers to thereby increase the fiber's resistance to fluid flow, thereby delaying radial fluid wicking and facilitating fluid wicking longitudinally.

* * * * *

UNITED STATES PATENT AND TRADEMARK OFFICE
CERTIFICATE OF CORRECTION

| | |
|---|---|
| PATENT NO. | : 9,707,135 B2 |
| APPLICATION NO. | : 14/204616 |
| DATED | : July 18, 2017 |
| INVENTOR(S) | : Sheldon et al. |

It is certified that error appears in the above-identified patent and that said Letters Patent is hereby corrected as shown below:

In the Claims

In Claim 4 at Column 18, Line 43, replace the "1" with --2--.

In Claim 16 at Column 19, Line 15, insert the word --an-- before the word "absorbent".

In Claim 19 at Column 19, Line 25, delete the word "wrapped".

Signed and Sealed this
Second Day of October, 2018

Andrei Iancu
*Director of the United States Patent and Trademark Office*